(12) United States Patent
Fukushima et al.

(10) Patent No.: US 10,357,145 B2
(45) Date of Patent: Jul. 23, 2019

(54) WIRE DRIVER FOR WIRE LINE AND ENDOSCOPE

(71) Applicant: FUJIFILM Corporation, Tokyo (JP)

(72) Inventors: Kimitake Fukushima, Ashigarakami-gun (JP); Yoshiyuki Kunuki, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 640 days.

(21) Appl. No.: 14/552,955

(22) Filed: Nov. 25, 2014

(65) Prior Publication Data

US 2015/0148598 A1      May 28, 2015

(30) Foreign Application Priority Data

Nov. 28, 2013   (JP) ................................. 2013-246689

(51) Int. Cl.
*A61B 1/00*     (2006.01)
*A61B 1/005*    (2006.01)
*A61B 1/018*    (2006.01)

(52) U.S. Cl.
CPC .......... *A61B 1/0057* (2013.01); *A61B 1/0052* (2013.01); *A61B 1/00098* (2013.01);
(Continued)

(58) Field of Classification Search
CPC .. A61B 1/0057; A61B 1/00098; A61B 1/0052
(Continued)

(56) References Cited

U.S. PATENT DOCUMENTS

| 4,164,333 A | * | 8/1979 | Hosaka | .................... G03B 1/08 |
| | | | | 396/17 |
| 4,924,724 A | * | 5/1990 | Yoshimura | ........... B63H 21/213 |
| | | | | 192/21 |

(Continued)

FOREIGN PATENT DOCUMENTS

| JP | 2003-144376 A | 5/2003 |
| JP | 2008-99743 A  | 5/2008 |
| JP | 2010-136737 A | 6/2010 |

OTHER PUBLICATIONS

Extended European Search Report for European Application No. 14195049.3, dated Apr. 2, 2015.
(Continued)

*Primary Examiner* — Alexandra L Newton
*Assistant Examiner* — Rynae Boler
(74) *Attorney, Agent, or Firm* — Birch, Stewart, Kolasch & Birch, LLP

(57) ABSTRACT

A side-viewing endoscope includes an elongated tube for entry in a body cavity for imaging. A wire line is contained in the elongated tube, for moving in an axial direction back and forth. A guide device is coupled with a distal end of the wire line, caused to shift between first and second positions by the wire line, for orientation in a direction crosswise to the axial direction upon being set in the second position. An input lever is disposed at a proximal end of the wire line, for moving the wire line in the axial direction. A cam mechanism is connected between the input lever and the wire line, for shifting the guide device at a first shift between the first position and an intermediate position, and shifting the guide device at a second shift smaller than the first shift between the intermediate and second positions.

6 Claims, 11 Drawing Sheets

(52) U.S. Cl.
CPC .......... *A61B 1/00188* (2013.01); *A61B 1/018* (2013.01); *Y10T 74/18176* (2015.01)

(58) Field of Classification Search
USPC ................................ 600/144, 146, 148, 107
See application file for complete search history.

(56) References Cited

U.S. PATENT DOCUMENTS

| | | | | |
|---|---|---|---|---|
| 5,060,632 | A | * | 10/1991 | Hibino ............... A61B 1/00039 348/65 |
| 5,683,412 | A | * | 11/1997 | Scarfone ............... A61B 17/29 606/205 |
| 2001/0044570 | A1 | | 11/2001 | Ouchi et al. |
| 2010/0191053 | A1 | * | 7/2010 | Garcia ............... A61B 1/00105 600/109 |
| 2013/0205937 | A1 | * | 8/2013 | Arai .................... A61B 1/0052 74/527 |

OTHER PUBLICATIONS

European Office Action, dated Nov. 24, 2016, for European Application No. 14 195 049.3.
Chinese First Office Action and Search Report dated Mar. 2, 2017, for Chinese Application No. 20140696768.7, with English translation of the Office Action only.
Chinese Office Action, dated Jul. 28, 2017, for corresponding Chinese Application No. 201410696768.7, with an English translation.

* cited by examiner

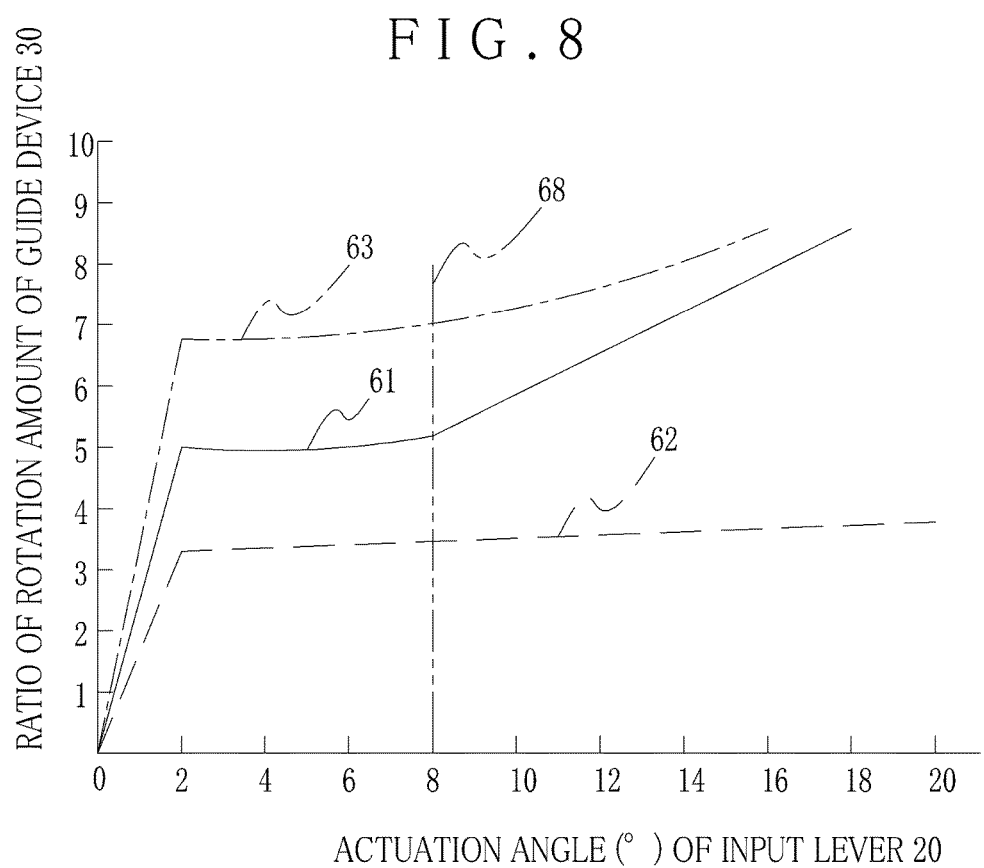

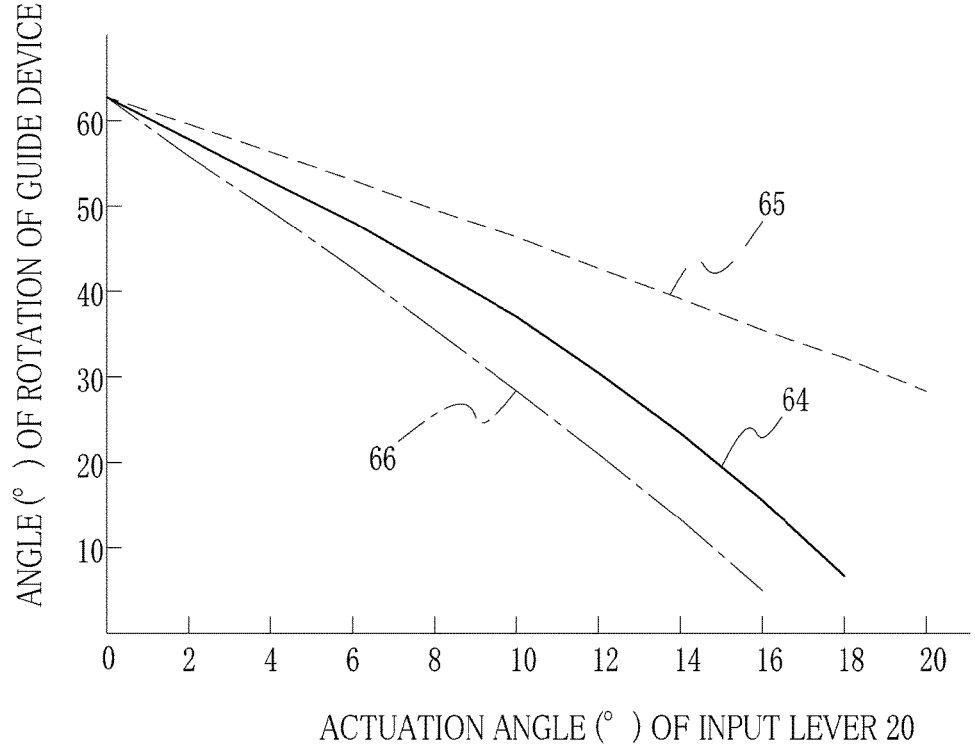

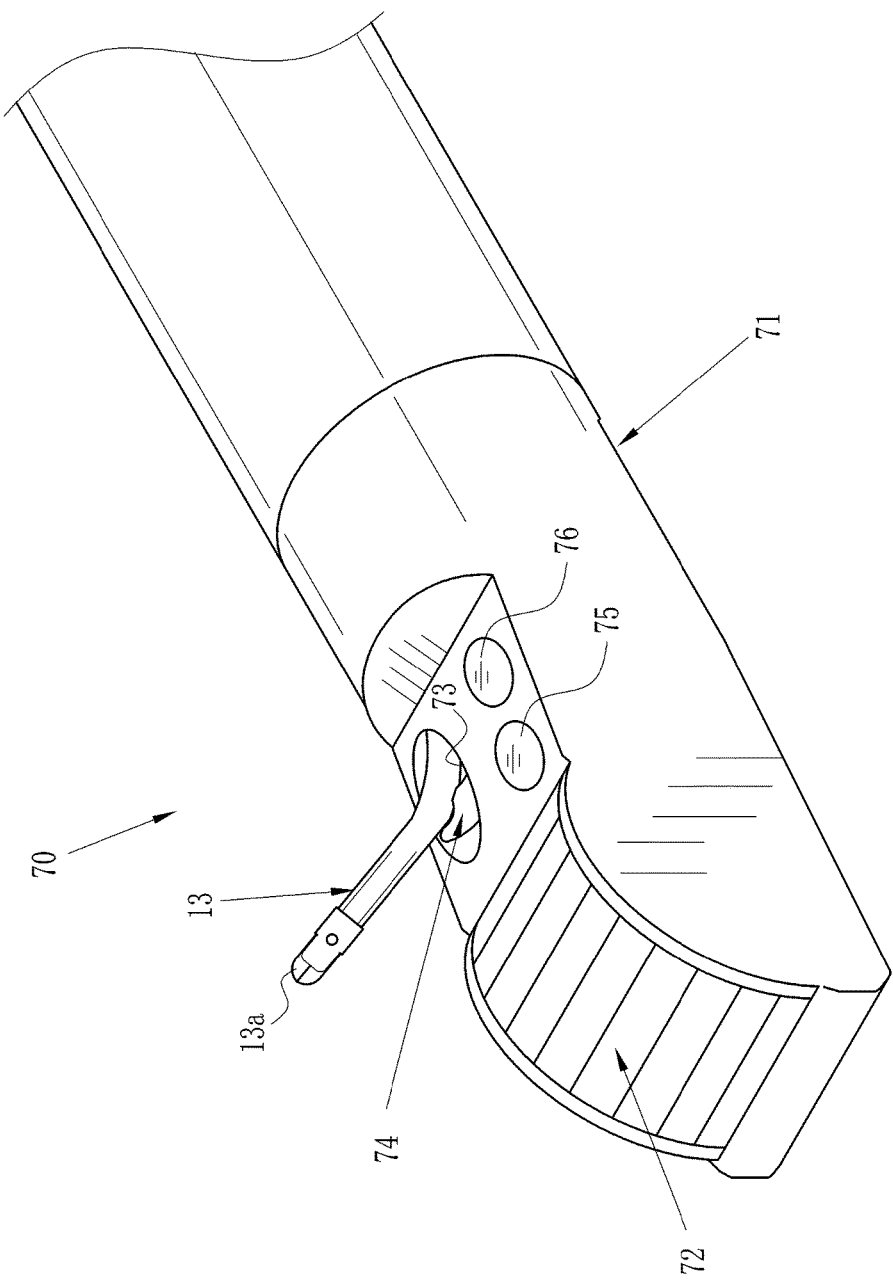

WIRE DRIVER FOR WIRE LINE AND ENDOSCOPE

CROSS-REFERENCE TO RELATED APPLICATION

This application claims priority under 35 USC 119 from Japanese Patent Application No. 2013-246689 filed 28 Nov. 2013, the disclosure of which is incorporated by reference herein.

BACKGROUND OF THE INVENTION

1. Field of the Invention

The present invention relates to a wire driver for a wire line and an endoscope. More particularly, the present invention relates to a wire driver for a wire line, with a simplified structure and operable for fine adjustment, and an endoscope.

2. Description Related to the Prior Art

An endoscope is widely used in the medical field for diagnosis. The endoscope includes an elongated tube and a grip handle. The elongated tube is entered in a body cavity of a patient. The grip handle is connected at a proximal end of the elongated tube. The grip handle has an externally operable device, such as an input lever and operation wheel. A movable part, which is disposed at a distal end of the elongated tube, is driven from a considerable distance by manipulating the externally operable device. Examples of the movable part include a guide device (direction changing device) for changing a direction of a medical instrument such as a biopsy device to protrude in a distal direction, and movable lens optics included in a zoom lens system disposed behind a viewing window.

JP-A 2010-136737 discloses a wire driver for push and pull of a wire line to drive the guide device from a considerable distance. The wire driver is incorporated in a side-viewing endoscope for imaging of an object in a lateral direction which is perpendicular to an axial direction of the elongated tube. In the wire driver, the position of the guide device is adjusted for a quick adjustment by transmitting rotation of the input lever to a pulley for a wire line without a decrease in the speed. Then the position of the guide device is adjusted for a fine adjustment by decreasing the speed of rotation, as the rotation of the input lever is transmitted to the pulley by use of gears.

In a view field of the endoscope, the medical instrument should precisely position at a target point of a lesion or the like. However, the guide device must be finely adjusted. In contrast, the find adjustment is not required in the outside of the view field. It is important to shift the guide device rapidly to return the medical instrument from the active position to the inactive position laid down to an instrument channel.

The endoscope according to JP-A 2010-136737 includes a first wheel for the quick adjustment and a second wheel for the fine adjustment. The first and second wheels must be changed over for the quick adjustment and fine adjustment of the guide device, so that operability for the adjustment is not high. Also, the endoscope of this document requires a speed decreasing device for the fine adjustment, so as to complicate the structure for the adjustment.

SUMMARY OF THE INVENTION

In view of the foregoing problems, an object of the present invention is to provide a wire driver for a wire line, with a simplified structure and operable for fine adjustment, and an endoscope.

In order to achieve the above and other objects and advantages of this invention, a wire driver for moving a wire line in an axial direction is provided, and includes an externally operable device. A drive lever pivotally moves upon operation of the externally operable device. A slider is movable in the axial direction, a proximal end of the wire line being coupled to the slider. A link portion transmits movement of the drive lever to the slider. A coupling shaft couples the drive lever to the link portion. A cam mechanism shifts the coupling shaft in a radial direction of pivotal movement of the drive lever.

Preferably, the externally operable device includes an input lever, retained on the drive lever, and rotatable by external operation.

Preferably, the cam mechanism includes a cam plate, and a cam groove, formed in the cam plate, for receiving the coupling shaft.

Preferably, the cam mechanism includes a first portion, and a second portion, disposed to continue from the first portion, for shifting the coupling shaft at a smaller shift amount than a shift amount of shift of the first portion for the coupling shaft.

Preferably, the first portion is a first groove portion of an arcuate shape defined about a rotational center of the drive lever. The second portion is a second groove portion directed to come nearer to the rotational center of the driver lever from the first portion.

Preferably, the cam mechanism further includes a shaft groove, formed in the drive lever, for receiving the coupling shaft, and pressing the coupling shaft upon rotation of the drive lever, to move the coupling shaft along the cam groove.

Preferably, furthermore, a slide channel supports the wire line movably in the axial direction. The wire line has a distal end coupled with the movable part, and shifts the movable part between the first and second positions in the axial direction. The cam mechanism shifts the movable part at a first shift amount between the first position and an intermediate position being defined between the first and second positions, and shifts the movable part at a second shift amount smaller than the first shift amount between the intermediate position and the second position.

Also, an endoscope is provided, and an elongated tube for entry in a body cavity for imaging of an object. A wire line is contained in the elongated tube, for moving in an axial direction back and forth. A movable part is coupled with a distal end of the wire line, caused to shift between first and second positions by the wire line. An externally operable device is disposed at a proximal end of the wire line, for moving the wire line in the axial direction. A cam mechanism is connected between the externally operable device and the wire line, for shifting the movable part at a first shift amount between the first position and an intermediate position being defined between the first and second positions, and shifting the movable part at a second shift amount smaller than the first shift amount between the intermediate position and the second position.

Preferably, furthermore, an instrument channel is formed through the elongated tube. A viewing window area is disposed in a tip device of the elongated tube, for imaging in the body cavity. A distal instrument opening is formed in the tip device, for protrusion of a medical instrument entered through the instrument channel. The movable part is a guide device, disposed between the distal instrument opening and the instrument channel, for shifting up from the first position to the second position, to guide the medical instrument into a view field of the viewing window area.

Preferably, the medical instrument starts entering the view field in case the guide device is in the intermediate position.

Preferably, furthermore, a link portion transmits movement of the externally operable device to the proximal end of the wire line. A coupling shaft couples the externally operable device to the link portion. The cam mechanism includes a first portion for shifting the coupling shaft. A second portion is disposed to continue from the first portion, for shifting the coupling shaft at a smaller shift amount than a shift amount of shift of the first portion for the coupling shaft.

In another preferred embodiment, furthermore, a zoom lens system is disposed in a tip device of the elongated tube, for imaging in the body cavity. The movable part is movable lens optics, included in the zoom lens system, caused to move by movement of the wire line. The first position is on a wide-angle side of the zoom lens system, and the second position is on a telephoto side of the zoom lens system.

Consequently, the wire driver can have a simplified structure and operable for fine adjustment, because the cam mechanism is used for readily shifting the driver lever for the wire line.

BRIEF DESCRIPTION OF THE DRAWINGS

The above objects and advantages of the present invention will become more apparent from the following detailed description when read in connection with the accompanying drawings, in which:

FIG. 8 is a graph illustrating a ratio of a rotation amount of the guide device to a rotation angle of the input lever;

FIG. 9 is a graph illustrating an rotation angle of the guide device relative to the rotation angle of the input lever;

FIG. 10 is a perspective view illustrating another preferred embodiment with an ultrasonic endoscope;

DETAILED DESCRIPTION OF THE PREFERRED EMBODIMENT(S) OF THE PRESENT INVENTION

Figure 1:
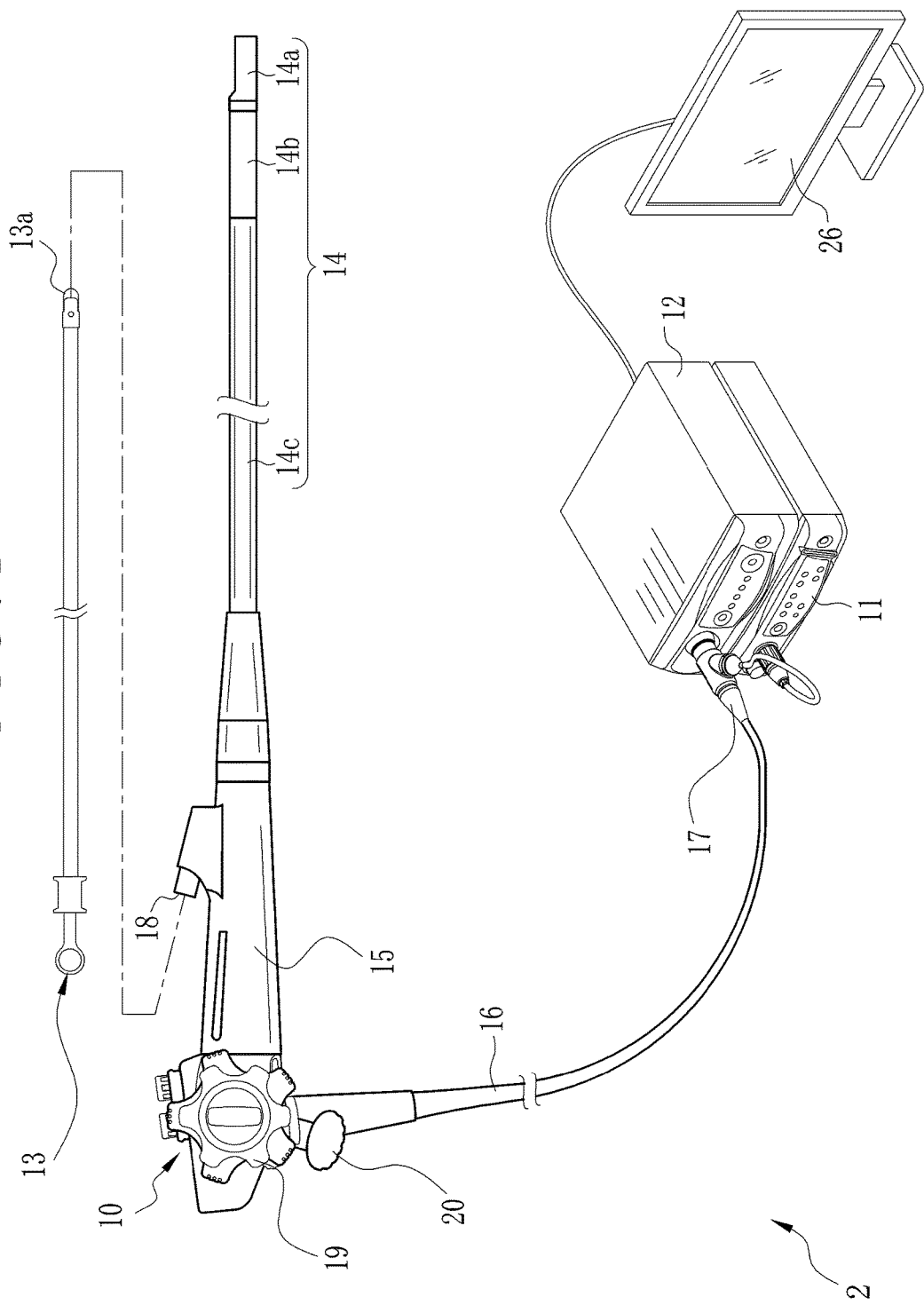
FIG. 1 is an explanatory view illustrating an endoscope system.

In FIG. 1, an endoscope system 2 includes an electronic endoscope 10, a processing apparatus 11, a light source apparatus 12 and a biopsy device 13 or medical instrument. The endoscope 10 includes an elongated tube 14, a grip handle 15 and a universal cable 16. The elongated tube 14 is entered in a body cavity of a patient. The grip handle 15 is connected to a proximal end of the elongated tube 14. The universal cable 16 is connected to the processing apparatus 11 or the light source apparatus 12. A connection plug 17 is coupled to a proximal end of the universal cable 16. The connection plug 17 is a composite type of connector for connection to the processing apparatus 11 and the light source apparatus 12.

The elongated tube 14 includes a tip device 14a, a steering device 14b and a flexible tube device 14c arranged in a proximal direction. The steering device 14b disposed at a proximal end of the tip device 14a, and includes a plurality of link elements connected in series. The flexible tube device 14c is disposed to extend from a proximal end of the steering device 14b to the grip handle 15.

An example of the endoscope 10 is a side-viewing endoscope, such as a duodenoscope. The endoscope 10 is entered through a mouth, esophagus and stomach and reaches a duodenum. The endoscope 10 is entered through a biliary tract of the duodenum to a common bile duct for imaging, sampling and/or treatment in medical diagnosis. There is an instrument channel formed in the endoscope 10 for the biopsy device 13. A proximal instrument opening 18 is formed in the grip handle 15 to receive entry of the biopsy device 13. The biopsy device 13 includes biopsy cups 13a and operates for sampling body tissue.

The grip handle 15 includes the proximal instrument opening 18, steering wheels 19 and an input lever 20 or operation lever as an externally operable device. In case the steering wheels 19 are rotated, control wires in the elongated tube 14 are moved back and forth, to steer the steering device 14b to the right and left and in upward and downward directions. Thus, the tip device 14a is directed in a desired direction.

Figure 2:
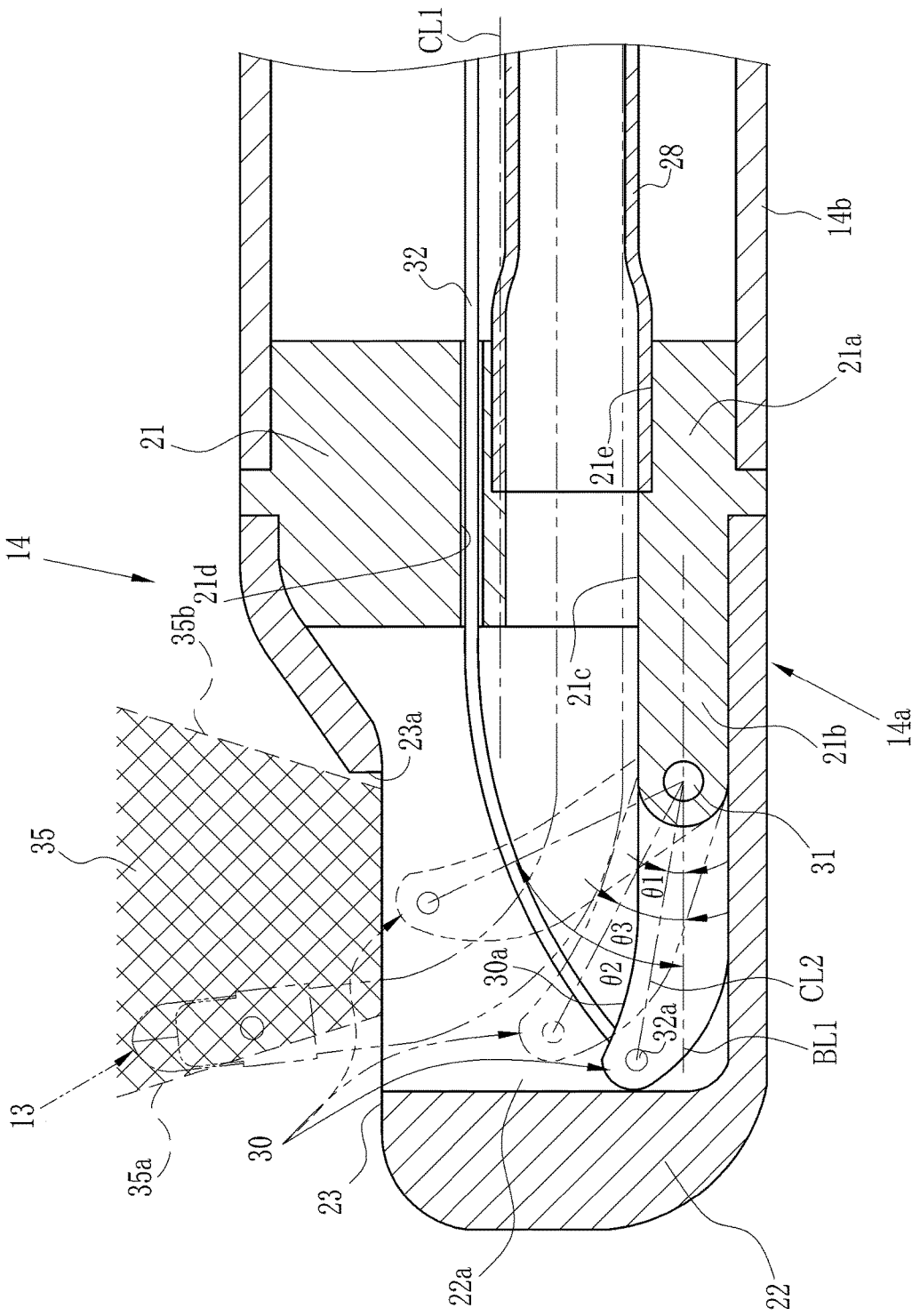
FIG. 2 is a vertical section illustrating a tip device.

In FIG. 2, the tip device 14a includes a head shell 21 and an end cap 22 fitted on the head shell 21.

Figure 3:
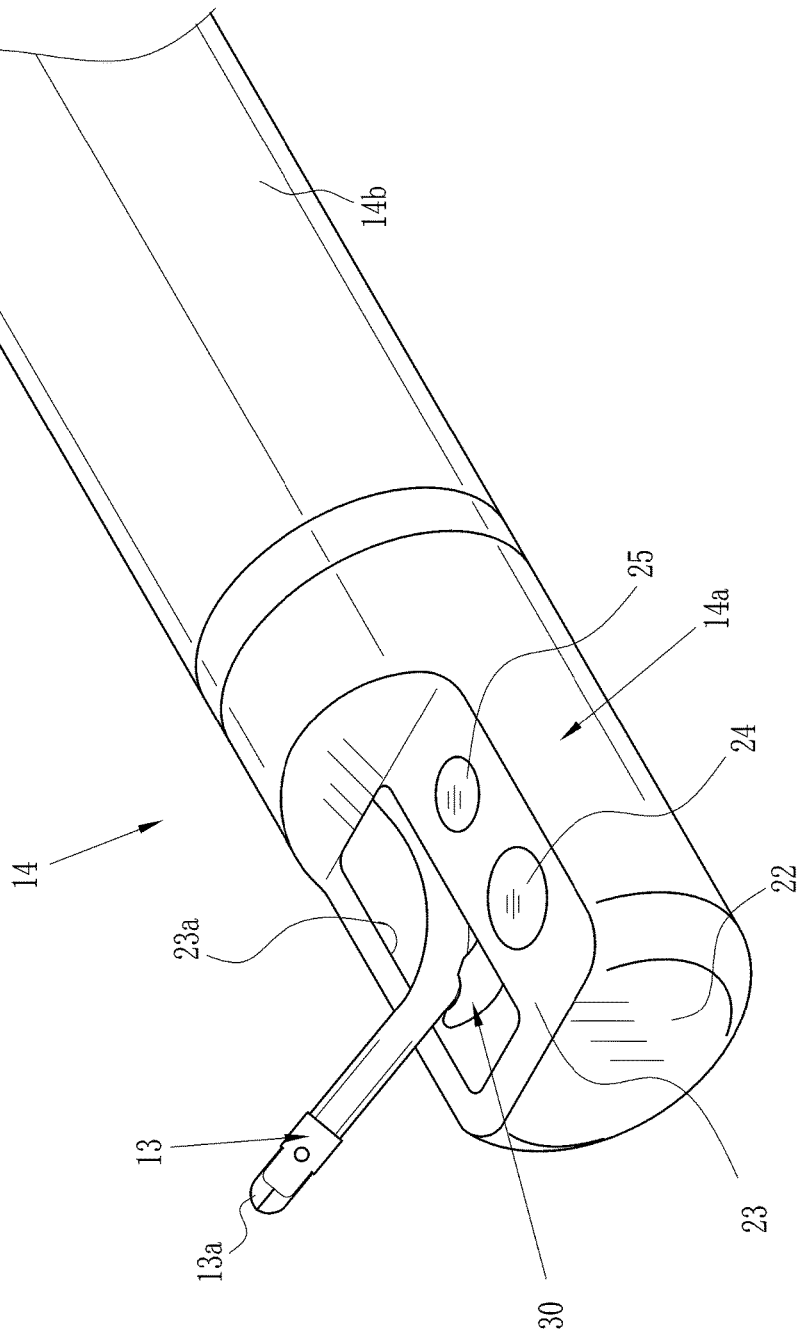
FIG. 3 is a perspective view illustrating the tip device.

In FIG. 3, a flat surface 23 is formed on an upper side of the end cap 22. A lighting window area 24 or lighting window means, and a viewing window area 25 or viewing window means are formed in the flat surface 23. The lighting and viewing window areas 24 and 25 are arranged in an axial direction of the elongated tube 14. A distal instrument opening 23a (lateral opening) is formed in the flat surface 23 beside the lighting and viewing window areas 24 and 25, and extends in parallel with the set of the lighting and viewing window areas 24 and 25. In FIG. 2, a guide chamber 22a is formed inside the end cap 22, and communicates with the distal instrument opening 23a. A guide device 30 (direction changing device) as a movable part is contained in the guide chamber 22a in a movable manner.

A lighting lens is disposed in the lighting window area 24. An exit end of a light guide device is positioned behind the lighting lens. A lens system for side-viewing is disposed in the viewing window area 25. An image sensor, such as a CCD, is disposed on a focal plane of the lens system. The lighting and viewing window areas 24 and 25 are the same as those used conventionally in known devices of side-viewing endoscopes, and are not described further. The processing apparatus 11 receives an image signal output by the CCD through a signal cable, and produces image data by image processing of various functions for the image signal. A monitor display panel 26 is driven according to the image data from the processing apparatus 11 connected with the signal cable, to display an image of the image data.

The head shell 21 includes a shell sleeve 21a of a cylindrical shape, and a support bracket 21b. A proximal end of the shell sleeve 21a is coupled with the steering device 14b. The support bracket 21b projects from a distal end of the shell sleeve 21a in the axial direction, and extends to a point aligned with the distal instrument opening 23a. A rotational support shaft 31 (rotational support portion) couples the guide device 30 to the support bracket 21*b* in a rotatable manner.

A receiving opening 21*c* and a slide hole 21*d* are formed through the shell sleeve 21*a* and disposed higher than the support bracket 21*b*. An inner shoulder 21*e* is formed in the receiving opening 21*c*. A flexible tube of an instrument channel 28 is fixedly fitted in the receiving opening 21*c* by use of the inner shoulder 21*e*. The instrument channel 28 extends from the elongated tube 14 through the grip handle 15 to the proximal instrument opening 18 in the axial direction. A wire line 32 or pull wire line is disposed to extend through the slide hole 21*d*. A pivot shaft 32*a* fixedly attaches a tip end of the wire line 32 to the guide device 30.

The guide device 30 is disposed between the distal instrument opening 23*a* and the instrument channel 28. The wire line 32 is pushed and pulled to shift the guide device 30 between a first position (inactive position) of the solid line, and a second position (active position) of the dotted line. An area between the first and second positions is a range where the guide device 30 is movable.

A guide surface 30*a* is located on the guide device 30 for the biopsy device 13. In the second position, the guide surface 30*a* guides the biopsy device 13 from the distal instrument opening 23*a* to the outside of the elongated tube 14 after passing the instrument channel 28 in the axial direction of the elongated tube 14. An advance direction of the biopsy device 13 is controlled by rotationally shifting the guide device 30 between the first and second positions.

The first position of the guide device 30 is so predetermined that a reference line BL1 parallel with the axial line CL1 intersects with a center line CL2 of the guide device 30 between the coupling shafts 31 and 32*a* at an intersection angle $\theta 1$ of 8 degrees. The second position of the guide device 30 is so predetermined that the reference line BL1 intersects with the center line CL2 at an intersection angle $\theta 2$ of 63 degrees. Thus, the range of movement of the guide device 30 is 55 degrees in the embodiment.

A view field 35 of the viewing window area 25 is hatched between dotted lines 35*a* and 35*b* in FIG. 3. The intermediate position of the guide device 30 (indicated by the phantom line) is so predetermined that the reference line BL1 intersects with the center line CL2 of the guide device 30 at an intersection angle $\theta 3$ of 42 degrees. Thus, the biopsy device 13 does not enter the view field 35 from the first position to the intermediate position, but is caused to enter the view field 35 from the intermediate position to the second position.

Figure 4:
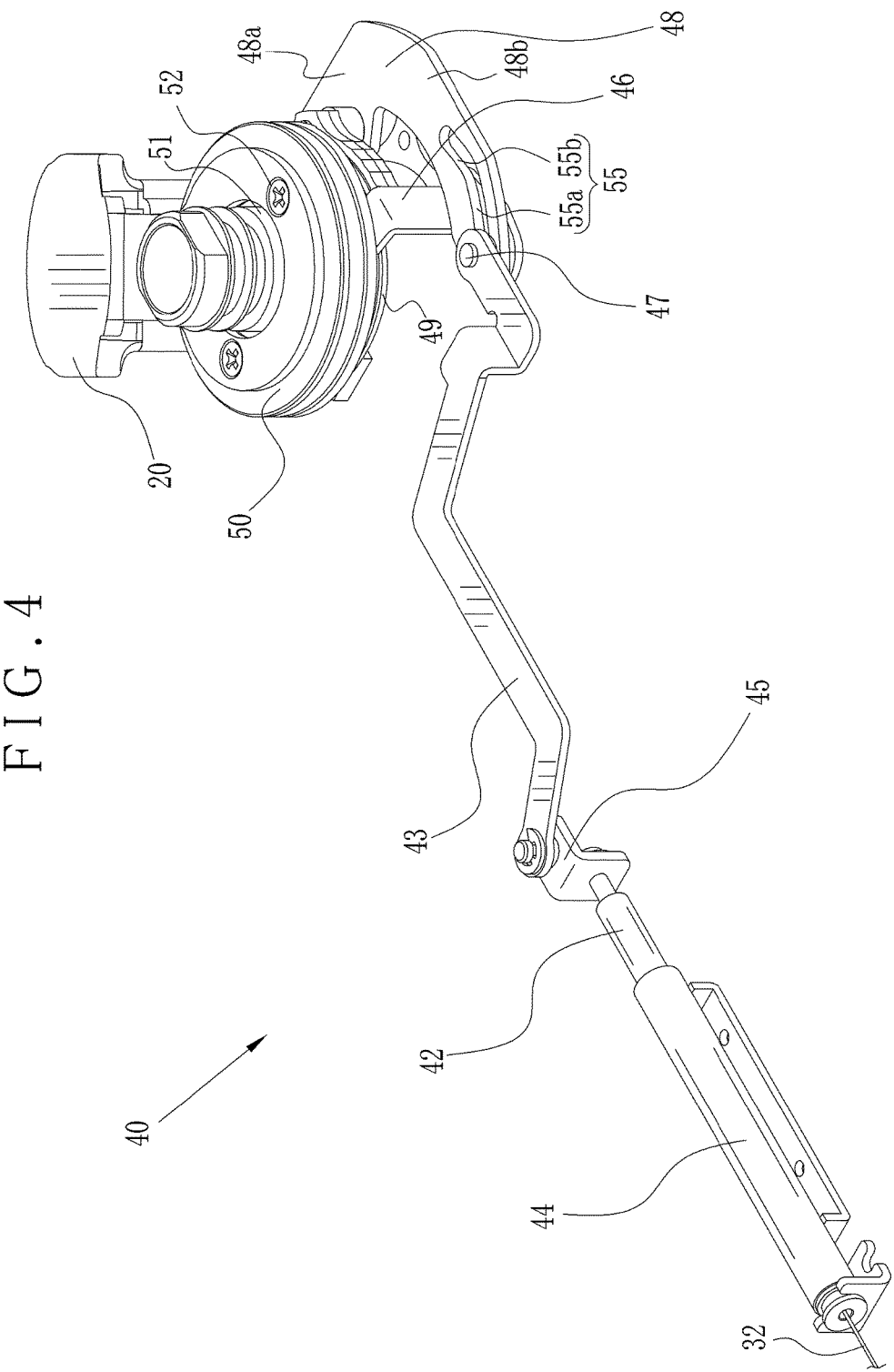
FIG. 4 is a perspective view illustrating a wire driver.

In FIG. 4, a wire driver 40 for push and pull moves the wire line 32 in distal and proximal directions at an upper end of the guide device 30, to shift the guide device 30 up and down. The wire driver 40 includes a rotatable wheel 41 or ring as a rotatable device (See FIG. 5), a slider 42, a link arm 43 or crank plate, a slide sleeve 44, a connection arm 45, a drive lever 46 (drive lever device), a cam shaft 47 as a coupling shaft, a cam plate 48 in a cam mechanism, a support device 49 and a mount ring 50.

Figure 5:
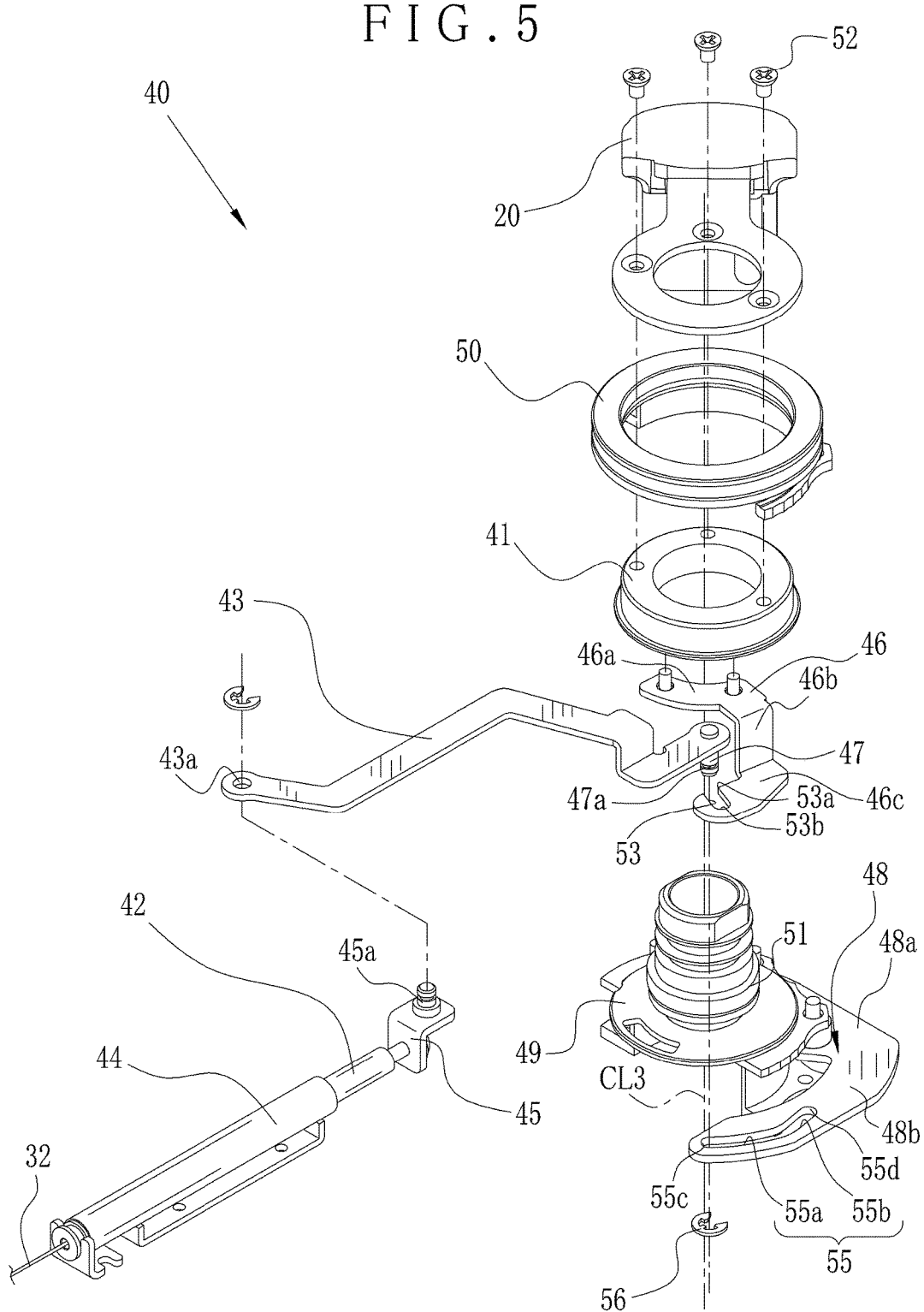
FIG. 5 is an exploded perspective view illustrating the wire driver.

In FIG. 5, the rotatable wheel 41 is disposed coaxially with a rotational shaft sleeve 51 on the support device 49, and rotatable around the shaft sleeve 51. The support device 49 and the mount ring 50 constitute a support unit for supporting the rotatable wheel 41. The mount ring 50 is disposed around an outer surface of the rotatable wheel 41, and fixed on the support device 49. The mount ring 50 keeps the rotatable wheel 41 on the support device 49 without drop. Note that an operable device of the invention is not limited to the rotatable wheel 41 of a circular shape, but can be a form supportable on the support unit. Although the support unit is constituted by the support device 49 and the mount ring 50, a support unit of a single piece can be provided.

Screws 52 as a retaining portion are fastened to fix the input lever 20 on the rotatable wheel 41. The support device 49 is attached fixedly to a housing of the grip handle 15. The shaft sleeve 51 has a central channel. A shaft of the steering wheels 19 (See FIG. 1) is received in and attached to the shaft sleeve 51, to keep the steering wheels 19 positioned.

In FIG. 5, screws are used to attach the drive lever 46 to a lower surface of the rotatable wheel 41, so that the drive lever 46 is rotatable together with the input lever 20 and the rotatable wheel 41.

The drive lever 46 includes an upper plate 46*a*, a side plate 46*b* and a lower plate 46*c* arranged in a crank shape as viewed laterally. The upper plate 46*a* is fixed on the lower surface of the rotatable wheel 41. A shaft groove 53 (slide groove) is formed in the lower plate 46*c*. A cam mechanism is constituted by the shaft groove 53 and the cam plate 48. The shaft groove 53 is disposed in a radial direction of the rotatable wheel 41, and has a first groove end 53*a* or groove opening. The cam shaft 47 is received in the shaft groove 53 in a linearly movable manner.

The cam plate 48 is disposed under the support device 49. The cam plate 48 is in an L shape and includes a linear portion 48*a* and a curved portion 48*b*. The linear portion 48*a* extends in a radial direction of the rotatable wheel 41. One end of the linear portion 48*a* is fixedly secured to a lower surface of the shaft sleeve 51. A second end of the linear portion 48*a* has the curved portion 48*b*. A cam groove 55 is formed in the curved portion 48*b*. The cam shaft 47 is received in and engaged with the cam groove 55 movably.

The cam groove 55 includes an arcuate first groove portion 55*a* and a linear second groove portion 55*b*. The first groove portion 55*a* is arcuate about a center of a center line CL3 of the shaft sleeve 51. The second groove portion 55*b* continues from the first groove portion 55*a*, and is directed to come nearer to a rotational center of the drive lever, in short, linearly along a chord of the arc of the first groove portion 55*a*. The first groove portion 55*a* is positioned to correspond to a second groove end 53*b* of the shaft groove 53 in a radial direction of the rotatable wheel 41 while the lower plate 46*c* of the drive lever 46 is attached to the cam plate 48. Thus, the cam shaft 47 is entered in a space of alignment of the cam groove 55 and the shaft groove 53.

The cam shaft 47 is attached to an end of the link arm 43 and projects downwards. A receiving groove 47*a* is formed at a lower end of the cam shaft 47. A mount ring 56 of an E-shape is fitted in the receiving groove 47*a* in the cam shaft 47 after entry in the shaft groove 53 and the cam groove 55, and keeps the cam shaft 47 in the shaft groove 53 and the cam groove 55 without drop. As the cam shaft 47 is movable through the shaft groove 53 and the cam groove 55, the cam shaft 47 causes coupling of the drive lever 46, the cam plate 48 and the link arm 43.

A connection hole 43*a* is formed in a second end portion of the link arm 43. A connection pin 45*a* of the connection arm 45 is received in the connection hole 43*a*. The connection arm 45 is disposed at a first end of the slider 42. The wire line 32 is coupled to a second end of the slider 42. The slider 42 is supported in the slide sleeve 44 in a slidable manner. The slide sleeve 44 is attached to a housing of the grip handle 15 fixedly.

Figure 6:
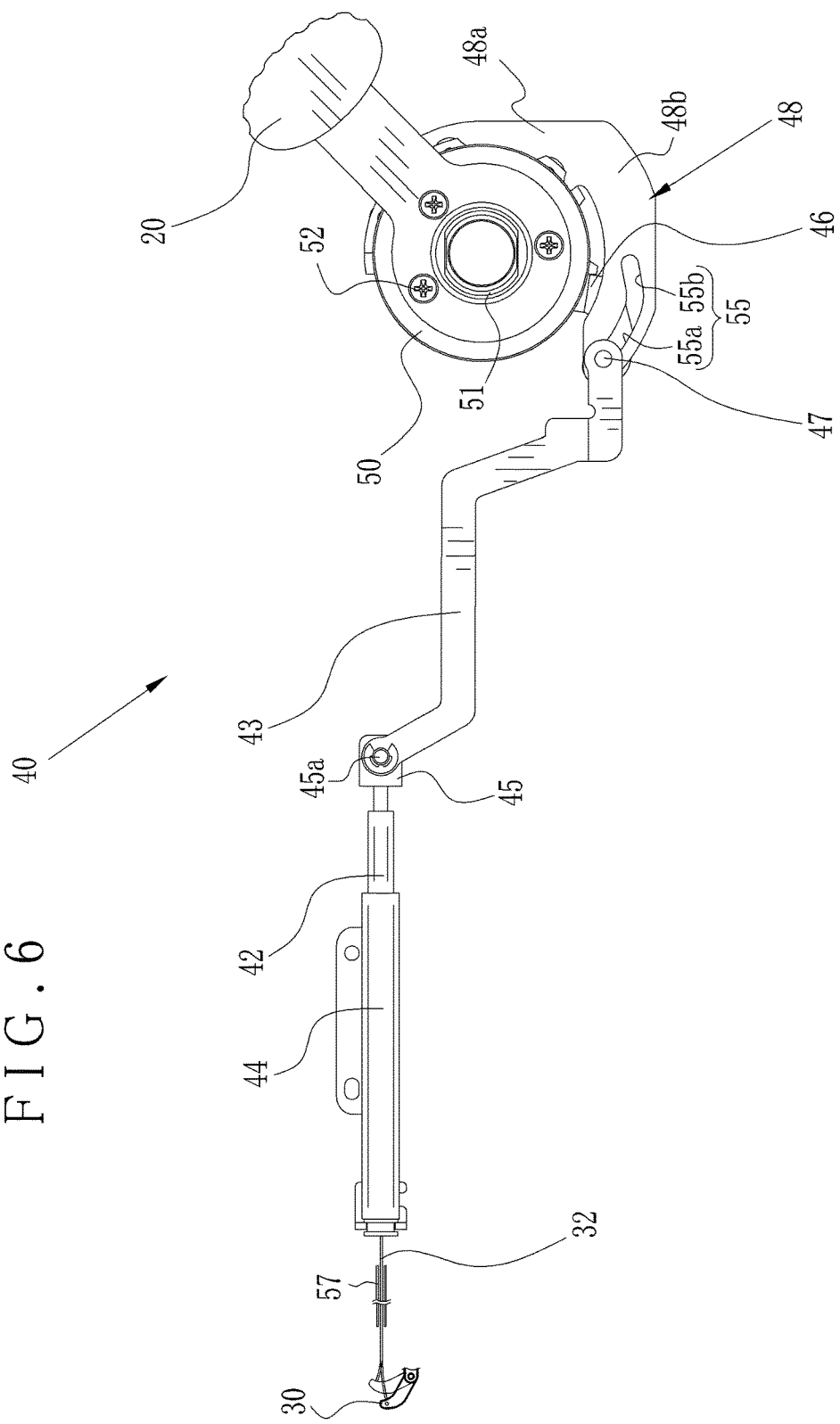
FIG. 6 is a plan illustrating a guide device and the wire driver.

In FIG. 6, a flexible sheath 57 with a slide channel contains the wire line 32. An example of the flexible sheath 57 includes a coil of a tightly wound wire, and a tube of a thermal compression type encapsulating the coil. The slider 42 and the link arm 43 convert the movement of the cam shaft 47 into a linear movement of the wire line 32 upon manipulation of the input lever 20. The cam shaft 47 is shifted in the cam groove 55 by the wall of the shaft groove 53 according to a rotational angle of the input lever 20. The cam shaft 47, while moved in the first groove portion 55a, moves at a shift amount according to the unit angle of rotation of the input lever 20. The link arm 43 moved according to the shift amount converts the movement into a linear movement of the slider 42. The cam shaft 47, while moved in the second groove portion 55b, moves at a shift amount smaller than in the first groove portion 55a in a direction of the slider 42 according to the unit angle of rotation of the input lever 20, owing to the inclination of the second groove portion 55b to the first groove portion 55a. Thus, the shift amount is changed between the states of movement of the cam shaft 47 in the first and second groove portions 55a and 55b.

In the present embodiment, the distal end of the wire line 32 is coupled to an end of the guide device 30 of the endoscope 10. In case the input lever 20 is rotated, the wire driver 40 causes the wire line 32 to move back and forth (push and pull), to swing the guide device 30. The biopsy device 13 is moved up or down by the guide device 30.

While the cam shaft 47 is in the first groove portion 55a, the guide device 30 becomes erect in a proportional manner to a rotational angle of the input lever 20. While the cam shaft 47 is in the second groove portion 55b, the shift amount of the wire line 32 is smaller than while the cam shaft 47 is in the first groove portion 55a. Thus, the guide device 30 becomes erect more slowly than while the camshaft 47 is in the first groove portion 55a. A time point of changeover between the first and second groove portions 55a and 55b is predetermined at a time point of entry of the biopsy device 13 into the view field 35 upon guiding with the guide device 30. The guide device 30 can be moved quickly outside the view field 35 proportionally to a shift of the input lever 20, but moved more slowly upon entry of the biopsy device 13 in the view field 35. It is possible to position the biopsy device 13 at a lesion or an object of interest precisely by fine shift of the erection of the guide device 30.

Figure 7A:
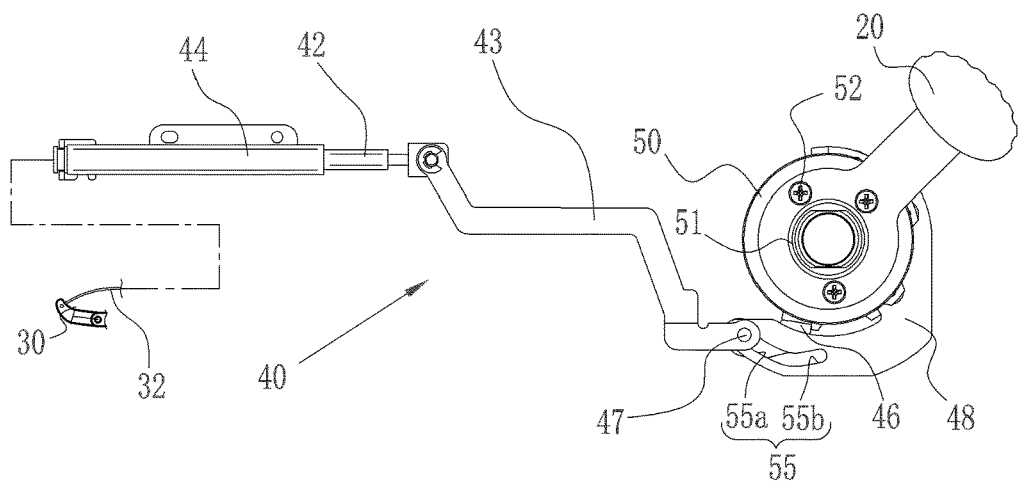
FIG. 7A is a plan illustrating the guide device in a first position (inactive position)
Figure 7B:
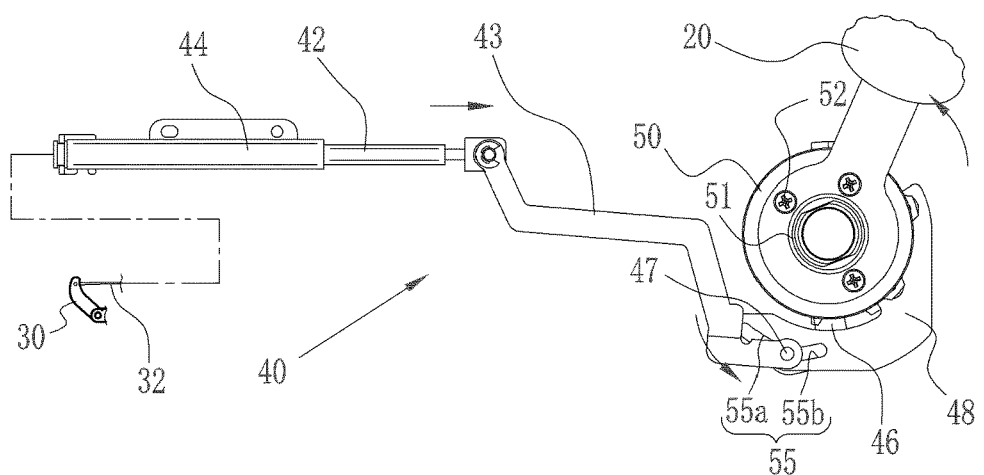
FIGS. 7B and 7C are plans illustrating the guide device in an intermediate position and second position (active position)
Figure 7C:
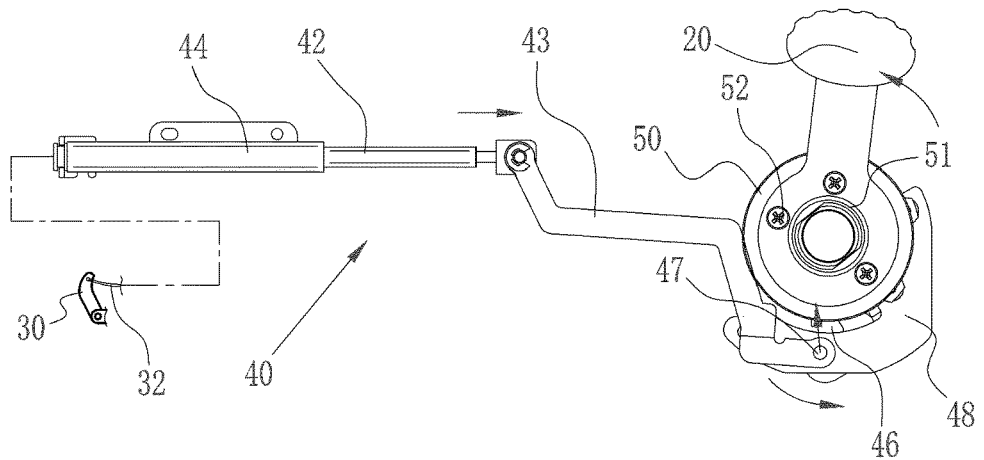

Movement of the wire driver 40 is described now by referring to FIGS. 7A, 7B and 7C. In the wire driver 40, the cam shaft 47 is received in the cam groove 55 as described above, and also received in the shaft groove 53. In case the rotatable wheel 41 is rotated by manipulating the input lever 20, the cam shaft 47 is shifted between end positions of the cam groove 55.

In FIG. 7A, the cam shaft 47 contacts one groove end 55c of the first groove portion 55a. The guide device 30 is in the first position. In FIG. 7B, the cam shaft 47 is moving from the first groove portion 55a to the second groove portion 55b. The guide device 30 is in the intermediate position. In FIG. 7C, the cam shaft 47 contacts one groove end 55d of the second groove portion 55b. The guide device 30 is in the second position.

While the cam shaft 47 moves in the first groove portion 55a in the arcuate shape, the rotatable wheel 41 rotates, and the camshaft 47 contacts the second groove end 53b of the shaft groove 53 in a constant position in a radial direction. Thus, the cam shaft 47 moves away from the slider 42 both in the axial direction and in the radial direction until the guide device 30 comes from the first position to the intermediate position upon passage of the cam shaft 47 in the first groove portion 55a.

While the cam shaft 47 moves in the second groove portion 55b of the linear shape, the rotatable wheel 41 rotates, and the cam shaft 47 moves along the shaft groove 53 inwards in the radial direction. The cam shaft 47 is pulled away from the slider 42 in the axial direction until the guide device 30 comes from the intermediate position to the second position as an end after passage of the cam shaft 47 in the second groove portion 55b. However, the cam shaft 47 moves toward the slider 42 in the radial direction. A shift amount of the cam shaft 47 is smaller than while the guide device 30 is from the first position to the intermediate position.

This being so, the shift amount of the end of the link arm 43 connected with the camshaft 47 is changed relative to a rotation amount of the input lever 20 while the input lever 20 rotates, namely upon passage of the cam shaft 47 at the point between the first and second groove portions 55a and 55b, owing to the cam mechanism between the input lever 20 and the link arm 43. Also, the shift amount of the slider 42 with the link arm 43 changes, and the shift amount of the wire line 32 changes. A ratio of the second rotation amount of the guide device 30 to the first rotation amount of the input lever 20 is changed during rotation from the first position to the second position. In passage of the cam shaft 47 in the first groove portion 55a, the ratio of the second rotation amount of the guide device 30 to the first rotation amount of the input lever 20 is large. In passage of the cam shaft 47 in the second groove portion 55b, the ratio of the second rotation amount of the guide device 30 to the first rotation amount of the input lever 20 is small. Note that the cam mechanism operates similarly also during rotation of the guide device 30 from the second position to the first position, in the same manner as FIGS. 7A-7C with the rotation of the guide device 30 from the first position to the second position. Upon passage of the cam shaft 47 at the point between the first and second groove portions 55a and 55b, or while the input lever 20 rotates, a change occurs in the ratio of the second rotation amount of the guide device 30 to the first rotation amount of the input lever 20.

In FIG. 8, an example of a ratio of the second rotation amount of the guide device 30 to a rotation angle of the input lever 20 in the endoscope 10 is illustrated. A graph curve 61 of the solid line denotes the second rotation amount of the guide device 30 per unit angle of 2 degrees of rotation of the input lever 20. A graph curve 62 of the broken line denotes the second rotation amount of the guide device of the known endoscope per unit angle of 2 degrees of rotation of the input lever 20. A graph curve 63 of the phantom line denotes the second rotation amount of the guide device of the known endoscope per unit angle of 2 degrees of rotation of the input lever 20 in a condition with a half amount of the first rotation amount of the input lever 20, in other words, in a condition where a ratio of the second rotation amount of the guide device to the first rotation amount of the input lever 20 is 2 times as high as the known endoscope. In FIG. 9, a graph curve 64 of the solid line denotes the second rotation amount of the guide device 30 relative to the rotation angle of the input lever 20 in the endoscope 10. A graph curve 65 of the broken line denotes the second rotation amount of the guide device relative to the rotation angle of the input lever 20 in the known endoscope. A graph curve 66 of the phantom line denotes the second rotation amount of the guide device relative to the rotation angle of the input lever 20 in the known endoscope, in a condition with a half amount of the first rotation amount of the input lever 20. Note that in FIGS. 8 and 9, the value of the angle of the input lever 20 on the horizontal axis is that of the input lever 20 with reference to zero degree at the time of the second position of the guide device. The value of a measurement result on the vertical axis is that measured upon rotating the input lever 20 from the state at the time of the second position of the guide device.

In FIGS. 8 and 9, the input lever 20 is actuated at an angle from 0 degree to 8 degrees (at a line 68 in FIG. 8), namely to shift the guide device 30 from the second position to the intermediate position. A ratio of the first rotation amount of the guide device 30 to the rotation angle of the input lever 20 is small and constant. In the present specification, being constant means a state of being constant or nearly constant. Furthermore, the input lever 20 is actuated at an angle from 8 degrees to 18 degrees, namely to shift the guide device 30 from the intermediate position to the first position. A ratio of the first rotation amount of the guide device 30 to the rotation angle of the input lever 20 is large, and gradually increased. In a known structure of the endoscope, a ratio of the first rotation amount of the guide device 30 to the rotation angle of the input lever is constant and smaller than that according to the embodiment at the time upon rotation of the guide device 30 from the second position to the first position. In the known endoscope, the first rotation amount of the input lever to move the guide device 30 from the second position to the first position is larger than the first rotation amount according to the embodiment. Should the first rotation amount be half as large as that of the known endoscope, the ratio of the first rotation amount of the guide device 30 to the rotation angle of the input lever is higher than that according to the embodiment, and is gradually increased. The first rotation amount of the input lever to shift the guide device 30 from the second position to the first position is smaller than the first rotation amount of the embodiment.

The operation of the endoscope 10 is described. The elongated tube 14 is entered in a body cavity of a patient. Biopsy sampling or examination is performed by viewing an object of interest in the monitor display panel 26. At first, the biopsy device 13 is entered into the instrument channel 28 through the proximal instrument opening 18 in the grip handle 15. The input lever 20 has not been manipulated. The guide device 30 is in the first position (inactive position). In case a distal end of the biopsy device 13 reaches the guide surface 30a of the guide device 30, the input lever 20 is rotated in the counterclockwise direction. The wire driver 40 is actuated to shift the guide device 30 from the first position to the second position (active position). While the guide device 30 is set between the intermediate and second positions, a ratio of the second rotation amount of the guide device 30 to the first rotation amount of the input lever 20 becomes small. The guide device 30 can be finely adjusted upon entry of the biopsy device 13 in the view field, to control a direction of advance of the biopsy device 13 with high precision.

In case the input lever 20 is rotated in the clockwise direction in the state of the second position of the guide device 30, the wire driver 40 operates to shift the guide device 30 from the second position to the first position. While the guide device 30 is set between the intermediate and second positions, a ratio of the second rotation amount of the guide device 30 to the first rotation amount of the input lever 20 becomes small owing to the cam mechanism. Thus, it is possible to control a direction of introducing the biopsy device 13 precisely, as the guide device 30 is finely adjusted upon entry of the biopsy device 13 in the view field.

The input lever 20 is rotated in the clockwise direction after the biopsy sampling or examination with the biopsy device 13. The ratio of the second rotation amount of the guide device 30 to the first rotation amount of the input lever 20 becomes large while the guide device 30 is between the intermediate and first positions. The guide device 30 shifts quickly upon movement of the biopsy device 13 out of the view field. The biopsy device 13 can be pulled out of the instrument channel 28 by quickly returning the biopsy device 13 in the axial direction of the elongated tube 14.

As described heretofore, the ratio of the second rotation amount of the guide device 30 to the rotation angle of the input lever is smaller in the known endoscope than in the present embodiment. The shift of the guide device 30 is slow even while the biopsy device 13 is disposed outside the view field. In contrast, the ratio of the second rotation amount of the guide device 30 to the rotation angle of the input lever is smaller in the present embodiment than in the known endoscope assuming that the first rotation amount is set half as large in the embodiment as in the known endoscope. Thus, the biopsy device 13 cannot be finely adjusted in the view field. However, it is possible in the present invention to adjust the guide device 30 finely while the biopsy device 13 is inside the view field and to adjust the guide device 30 quickly while the biopsy device 13 is outside the view field, simply by utilizing the cam plate. Also, operability can be high, as the single input lever is manipulated for fine adjustment of the guide device 30 inside the view field and quick adjustment of the guide device 30 outside the view field.

Note that it is further possible additionally to use a torsion coil spring with the pivot shaft 32a for biasing the guide device 30 toward the first position, in cooperation with the wire line 32 for moving the guide device 30 back and forth.

The present invention is not limited to the above embodiment of the side-viewing endoscope. In FIG. 10, another preferred embodiment with an ultrasonic endoscope is illustrated. The endoscope includes an elongated tube 70 and a tip device 71. The tip device 71 has an ultrasonic imaging device 72 with an array of ultrasonic transducers, a distal instrument opening 73, a guide device 74 (direction changing device) as a movable part, a viewing window area 75 or viewing window means, and a lighting window area 76 or lighting window means. The distal instrument opening 73 is disposed on a proximal side from the ultrasonic imaging device 72. The guide device 74 changes a direction of the biopsy device 13 from the distal instrument opening 73 to the outside of the elongated tube 70. A shifting structure of the guide device 74 includes the input lever 20, the wire line 32 and the wire driver 40 in a manner similar to the above embodiment.

In the above embodiments, the externally operable device for the wire driver 40 is the input lever. However, a knob, wheel, dial or the like of a circular shape can be an externally operable device for rotational manipulation. In the above embodiments, the biopsy device 13 is a cup type. However, a medical device can be other devices for imaging, sampling and/or treatment, such as a forceps of a clip type, high frequency knife, snare wire, injection needle and the like. The endoscope 10 is an instrument for medical use in the above embodiments, but can be a device for industrial use.

Figure 11:
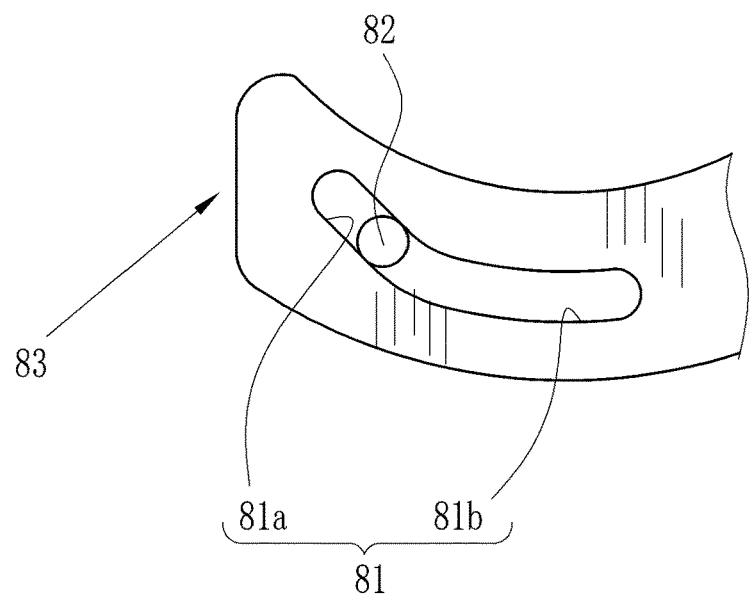
FIG. 11 is a plan illustrating another preferred cam groove.

In the above embodiments, the shift of the movable part with the wire line is changed over from the quick shift to the fine shift. In FIG. 11, a preferable wire driver is illustrated. A cam mechanism includes a cam shaft 82 and a cam plate 83. A cam groove 81 is formed in the cam plate 83, and includes a linear groove portion 81a and an arcuate groove portion 81b. The cam shaft 82 is engaged with the cam groove 81 in a movable manner. The linear groove portion 81a is positioned with an inclination outwards in a radial direction relative to a rotational center of the input lever. The arcuate groove portion 81b continues from the linear groove portion 81a, and extends arcuately about a rotational center of the input lever. Thus, a movable part in connection with the cam shaft 82 shifts at a small shift amount relative to a unit angle of rotation of the input lever while the cam shaft 82 moves in the linear groove portion 81a, but shifts at a large shift amount relative to the unit angle of rotation of the input lever while the cam shaft 82 moves in the arcuate groove portion 81b.

Figure 12:
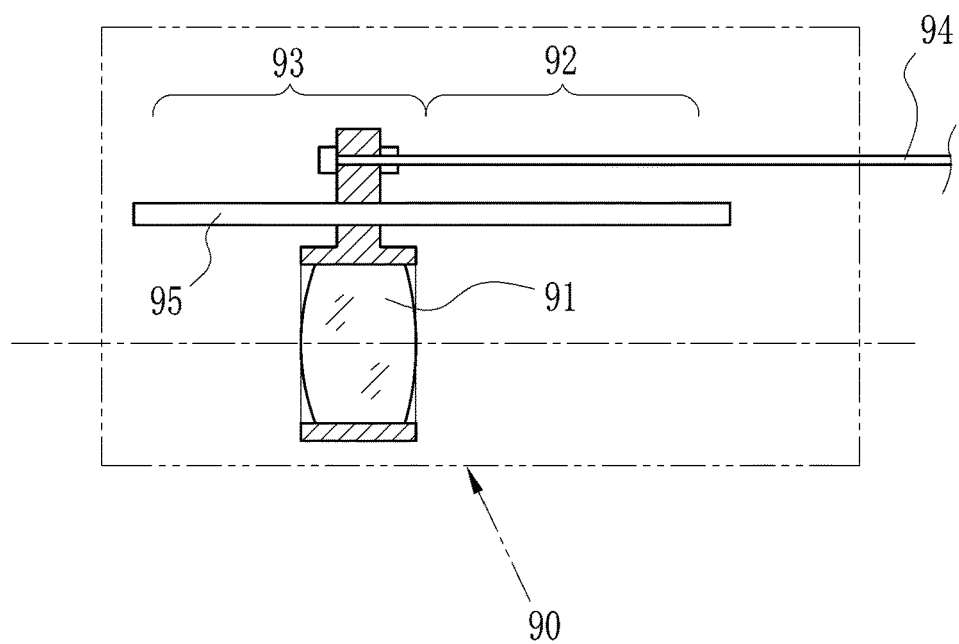
FIG. 12 is a side elevation illustrating another preferred embodiment with a zoom lens system.

In the above embodiment, the movable part to be moved by the wire line is the guide device. However, other examples of movable parts in the endoscope 10 can be moved by the construction of the invention. In FIG. 12, a zoom lens system 90 for the endoscope 10 includes movable lens optics 91 as a movable part. A wire driver moves in the movable lens optics 91 in a wide angle area 92 and a telephoto area 93. In the wide angle area 92, the movable lens optics 91 are moved quickly, as a depth of field is large in the wide angle area 92. In the telephoto area 93, the movable lens optics 91 are moved finely, as a depth of field is smaller in the telephoto area 93. A wire line 94 or pull wire line in FIG. 12 is attached to the movable lens optics 91. A guide rod 95 guides the movable lens optics 91 linearly. The endoscope 10 has the elongated tube 14 and the grip handle 15 in the same manner as the above embodiment. The movable lens optics 91 are moved between a wide-angle side and a telephoto side by the wire line 94. Furthermore, a coil spring can be additionally used with the wire line 94 for biasing the movable lens optics 91 toward the wide-angle side or the telephoto side.

In the above embodiment, the cam groove has the first and second groove portions. However, three or more groove portions can be included in a cam groove, to change over a moving speed of the wire line in three steps or more. In the above embodiments, the first groove portion is arcuate, the second groove portion being linear. However, a shape of a cam groove is not limited to this structure. It is possible to control the moving speed of the wire line in a more complicated sequence.

In the above embodiments, the link arm 43 is coupled to the slider 42. However, an end of the link arm 43 can be directly coupled to the end of the wire line 32 without using the slider 42. In the above embodiments, the slide sleeve 44 contains the slider 42 and enables the slider 42 to move only in the axial direction. However, it is possible to use a slide channel to enable the wire line 32 to move only in the axial direction without use of the slider 42.

In the above embodiments, the wire driver is used for the endoscope. However, a wire driver of the invention can be used for a probe or other apparatuses having a wire line, for medical use or for diagnosis.

In a preferred embodiment mode of the present invention, a rotational support portion supports a proximal end of the movable part in a rotatable manner with respect to the axial direction. An angle of the movable part with reference to the axial direction is larger upon being set in the second position than upon being set in the first position.

Also, the wire line is movable between distal and proximal positions, and the movable part is in the first position in case the wire line is in the distal position, and is in the second position in case the wire line is in the proximal position.

Also, the movable part is a guide device for guiding and erecting a distal end of a medical instrument being advanced.

In another preferred embodiment mode of the present invention, the movable part is movable in the axial direction between the first and second positions.

Also, the wire line is movable between distal and proximal positions, and the movable part is in the second position in case the wire line is in the distal position, and is in the first position in case the wire line is in the proximal position.

Also, the movable part is movable lens optics in a zoom lens system.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope comprising:
    an elongated tube for entry in a body cavity for imaging of an object;
    a wire line, contained in said elongated tube, for moving in an axial direction back and forth;
    a movable part, coupled with a distal end of said wire line, caused to shift between first and second positions by said wire line;
    an externally operable device, disposed at a proximal end of said wire line, for moving said wire line in said axial direction;
    a drive lever for pivotally moving upon operation of said externally operable device; and
    a cam mechanism, connected between said externally operable device and said wire line, configured to shift said movable part, during the pivotal movement of said drive lever by the operation of said externally operable device, at a first shift amount between said first position and an intermediate position being defined between said first and second positions, and shifting said movable part at a second shift amount smaller than said first shift amount between said intermediate position and said second position,
    the first shift amount and the second shift amount being defined for a unit operation amount of the externally operable device,
    the endoscope further comprising:
    a link portion for transmitting movement of said externally operable device to said proximal end of said wire line; and
    a coupling shaft for coupling said externally operable device to said link portion, said cam mechanism including:
    a cam plate; and
    a cam groove for receiving said coupling shaft, said cam groove being formed in said cam plate,
    wherein said cam groove includes:
    a first groove portion for shifting said coupling shaft, said first groove portion having an arcuate shape whose center is substantially coincident with a rotational center of said drive lever; and
    a second groove portion for shifting said coupling shaft at a smaller shift amount than a shift amount of said coupling shaft in said first groove portion, said second groove portion being disposed to continue from said first groove portion and directed to come nearer to said rotational center of said driver lever from said first groove portion.

2. The endoscope as defined in claim 1, further comprising:
- an instrument channel formed through said elongated tube;
- a viewing window area, disposed in a tip device of said elongated tube, for imaging in said body cavity;
- a distal instrument opening, formed in said tip device, for protrusion of a medical instrument entered through said instrument channel;
- wherein said movable part is a guide device, disposed between said distal instrument opening and said instrument channel, for shifting up from said first position to said second position, to guide said medical instrument into a view field of said viewing window area.

3. The endoscope as defined in claim 2, wherein said medical instrument starts entering said view field in case said guide device is in said intermediate position.

4. The endoscope as defined in claim 1, further comprising a zoom lens system, disposed in a tip device of said elongated tube, for imaging in said body cavity;
- wherein said movable part is movable lens optics, included in said zoom lens system, caused to move by movement of said wire line;
- said first position is on a wide-angle side of said zoom lens system, and said second position is on a telephoto side of said zoom lens system.

5. The endoscope as defined in claim 1, wherein said cam mechanism shifts said movable part between said first and second position during the operation of said externally operable device.

6. The endoscope as defined in claim 1, wherein said cam mechanism shifts said movable part between said first and second positions while said elongated tube is inserted in the body cavity.

* * * * *